(12) United States Patent
Schwarzlos-Sooprayen et al.

(10) Patent No.: US 12,251,213 B2
(45) Date of Patent: Mar. 18, 2025

(54) AUTOMATIC EAR IMPRESSION CLASSIFICATION

(71) Applicant: SONOVA AG, Stäfa (CH)

(72) Inventors: Jana-Kosima Schwarzlos-Sooprayen, Stäfa (CH); Markus Leuthold, Stäfa (CH)

(73) Assignee: Sonova AG, Staefa (CH)

( * ) Notice: Subject to any disclaimer, the term of this patent is extended or adjusted under 35 U.S.C. 154(b) by 1021 days.

(21) Appl. No.: 17/196,735

(22) Filed: Mar. 9, 2021

(65) Prior Publication Data

US 2021/0282666 A1 Sep. 16, 2021

(30) Foreign Application Priority Data

Mar. 11, 2020 (EP) ..................................... 20162491

(51) Int. Cl.
*G06F 30/20* (2020.01)
*A61B 5/00* (2006.01)
(Continued)

(52) U.S. Cl.
CPC .......... *A61B 5/1077* (2013.01); *A61B 5/6815* (2013.01); *G06F 30/20* (2020.01); *G06V 20/64* (2022.01); *G06F 2218/08* (2023.01); *G06F 2218/12* (2023.01); *G06V 2201/03* (2022.01); *H04R 25/658* (2013.01); *H04R 2225/77* (2013.01)

(58) Field of Classification Search
CPC ..... A61B 5/1077; A61B 5/6815; G06F 30/20; G06F 2218/08; G06F 2218/12; G06V 20/64; G06V 2201/03; H04R 2225/77; H04R 25/658

USPC ............................................................ 703/2
See application file for complete search history.

(56) References Cited

U.S. PATENT DOCUMENTS 8,064,731 B2 * 11/2011 Zouhar ................. B33Y 50/00
700/98
8,224,094 B2 7/2012 Melkisetoglu et al.
(Continued)

FOREIGN PATENT DOCUMENTS

EP 1345470 11/2006
WO 2013149645 10/2013

OTHER PUBLICATIONS

Extended European Search Report received in EP Application No. EP20162491.3 on Jul. 27, 2020.
(Continued)

*Primary Examiner* — John E Johansen
(74) *Attorney, Agent, or Firm* — ALG Intellectual Property, LLC

(57) ABSTRACT

An illustrative method for checking a usability of an impression model of a human ear includes determining an estimated shape model of the human ear by adapting a statistical shape model to the impression model, wherein the statistical shape model has been determined from a plurality of impression models of a plurality of human ears and wherein the statistical shape model has at least one impression feature, which is mapped to an estimated impression feature of the estimated shape model; determining a feature classification from the estimated impression feature; and when the feature classification is within an allowed feature classification range, rating the impression model as usable.

14 Claims, 2 Drawing Sheets

(51) Int. Cl.
*A61B 5/107* (2006.01)
*G06V 20/64* (2022.01)
*H04R 25/00* (2006.01)

(56) References Cited

U.S. PATENT DOCUMENTS

| | | |
|---|---|---|
| 8,229,180 B2 | 7/2012 | Baloch et al. |
| 2004/0107080 A1* | 6/2004 | Deichmann ............. A61F 11/08 |
| | | 703/6 |
| 2008/0143712 A1* | 6/2008 | McBagonluri ....... H04R 25/658 |
| | | 345/619 |
| 2008/0222564 A1 | 9/2008 | Bindner et al. |
| 2009/0116731 A1 | 5/2009 | Melkisetoglu et al. |
| 2009/0296980 A1* | 12/2009 | Yi ........................... G06T 7/579 |
| | | 382/100 |
| 2015/0073262 A1* | 3/2015 | Roth .................... A61B 5/0084 |
| | | 600/407 |
| 2020/0159878 A1* | 5/2020 | Zhang ................. H04R 25/658 |

OTHER PUBLICATIONS

Paulsen, et al., "Building and Testing a Statistical Shape Model of the Human Ear Canal", 2022.

\* cited by examiner

AUTOMATIC EAR IMPRESSION CLASSIFICATION

RELATED APPLICATIONS

The present application claims priority to EP Patent Application No. 20162491.3, filed Mar. 11, 2020, the contents of which are hereby incorporated by reference in their entirety.

BACKGROUND INFORMATION

Hearing devices are generally small and complex devices. Hearing devices can include a processor, microphone, speaker, memory, housing, and other electronical and mechanical components. Some example hearing devices are Behind-The-Ear (BTE), Receiver-In-Canal (RIC), In-The-Ear (ITE), Completely-In-Canal (CIC), and Invisible-In-The-Canal (IIC) devices. A user can prefer one of these hearing devices compared to another device based on hearing loss, aesthetic preferences, lifestyle needs, and budget.

Some custom hearing devices need an ear impression as a basis for the production. The ear impression may be made by a hearing care professional in order to fulfil the requirements for the appropriate custom product. Afterwards, the impression is usually shipped to the hearing instrument manufacturer and the production process starts. The ear impression may be digitized with an impression scanner and subsequently the custom product may be modelled, printed and assembled.

At the hearing instrument manufacturer, the quality of the ear impression is assessed by an operator before the manufacturing and codes for the quality of the ear impressions or parts thereof may be input into a manufacturing system. The drawback of this coding process is, that the quality rating is dependent on the training the operators receive. The coding may depend on the subjective assessment of the operator.

Another drawback is, that only by looking at the ear impression and by defining the quality of the ear impression, the operator is not able to distinguish whether the ordered custom product can be built out of the ear impression or not. Even if an ear impression provides all relevant features, it may be that the ear canal is too thin for a deep-fitting hearing device or the shape of the canal only allows for specific shell styles of the hearing device.

WO 2013 149 645 A1 describes a method of estimating the shape of an individual ear, wherein at least part of the shape of the individual ear is determined by measurement, a predefined template shape determined by statistical analysis of a plurality of previously measured ear shapes is taken and the estimated shape is generated therefrom.

BRIEF DESCRIPTION OF THE DRAWINGS

Below, embodiments of the present invention are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION

Figure 1:
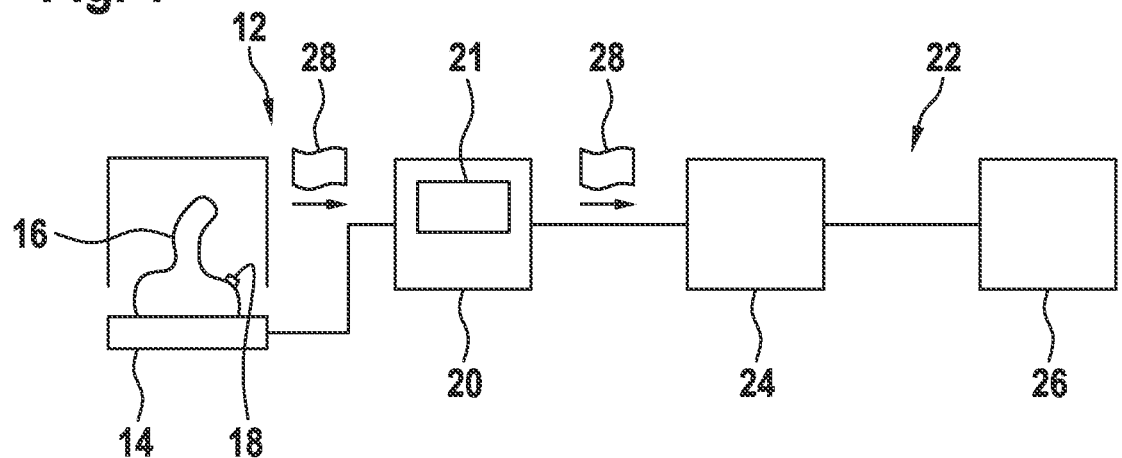
FIG. 1 schematically shows a system according to an embodiment.

Described herein are a method, a computer program, a computer-readable medium and a system for checking a usability of an impression model of a human ear.

Embodiments described herein simplify, improve and objectify the assessment of ear impressions and/or impression models. In some examples, features described herein improve the manufacturing process of a hearing device.

These embodiments are achieved by the subject-matter of the independent claims. Further exemplary embodiments are evident from the dependent claims and the following description.

A first aspect relates to a method for checking a usability of an impression model of a human ear. The method may be automatically performed, for example by a computing device and/or a system with such a computing device.

The usability may be checked with respect to, whether it is possible to manufacture a hearing device or at least a part of the hearing device based on the impression model of and/or of an ear impression from which the impression model was made.

The impression model of the human ear may be made by scanning interior and outer parts of the human ear with a scanner or may scan an ear impression of the human ear. The ear impression may be made by a hearing care specialist by filling material into the ear, which then hardens. The ear impression may be or may comprise a block of material, which is a negative imprint of parts of the human ear.

The impression model may be a file, which may be generated by a scanner. The impression model may be based and/or may comprise a point cloud produced by the scanner. For example, the impression model may comprise points with three coordinates and/or facets. The impression model may be encoded in the STL (stereolithography) file format. The impression model may comprise a plurality of three-dimensional points indicating a surface of the human ear and/or the impression model may comprise a wire frame model of this surface. The surface of the human ear also may be defined by the surface of an ear impression.

According to an embodiment, the method further comprises: determining an estimated shape model by adapting a statistical shape model to the impression model, wherein the statistical shape model has been determined from a plurality of impression models of a plurality of human ears and wherein the statistical shape model has at least one impression feature (which may model a feature of the impression model and/or the human ear), which feature is mapped to an estimated impression feature of the estimated shape model.

The impression model may be adapted to a statistical shape model and an estimated shape model may be generated. The statistical shape model may comprises a wire frame model, i.e. three-dimensional points and facets formed from the three-dimensional points indicating a surface of an average impression model and/or average ear surface. A plurality of impression models of a plurality of human ears may have been used to generate the statistical shape model.

The adaption of the impression model to the statistical shape model may be performed by deforming the statistical shape model (for example by moving its points), such that an objective function, which measures a difference between the impression model and the deformed statistical shape model, is minimized. For example, a method for determining an estimated shape model from a statistical shape model is described by WO 2013149645 A1, which is incorporated by reference. As the statistical shape model, the estimated shape model may comprise a wire frame model.

Additionally, in the statistical shape model, one or more impression features are encoded. An impression feature may be related to specific points, facets, areas, parts, etc. of the statistical shape model. The impression feature comprises a wire frame model of a part of the human ear and/or the estimated shape model. Due to the adaption process of the impression model to the estimated shape model, such an impression feature may be mapped from the statistical shape model to the estimated shape model. In such a way, features that have been selected as important in the statistical shape model may be identified in the impression model.

The one or more impression features may be encoded as additional data objects in the statistical shape model, which may reference points and/or facets in a wire frame model of the statistical shape model. An impression feature also may comprise a function, which, based on geometric relations encoded in the statistical shape model, outputs specific geometric values, such as a curvature of a part of the impression model.

According to an embodiment, the method further comprises: determining a feature classification from the estimated impression feature. From the one or more estimated impression features, one or more feature classifications of the specific features may be calculated. It may be that the statistical shape model has a plurality of impression features, which are mapped to estimated impression features. For each of these estimated impression features, an impression classification may be determined.

The feature classification of an impression feature may be a number calculated from the impression feature. One simple classification is, whether the feature was found in the impression model or not. For example, one impression feature may be a part of the ear channel (or an impression thereof), when this part has been shrunk to nearly a point or a volume smaller than a predefined size, the classification may be that this part is not there. Otherwise it may be classified as being there. There may be feature classifications based on discrete values, such as a size classified from 0 to 10 as integer. There may be feature classifications based on continuous values, such as a maximal and/or minimal inner diameter of the ear channel at a specific location.

According to an embodiment, the method further comprises: when the feature classification is within an allowed feature classification range, rating the impression model as usable. The one or more feature classifications are chosen, such that they predict, whether the impression model and/or a possible ear impression usable for manufacturing a hearing device or a part of the hearing device, such as an ear part or shell of an in-the-ear hearing device. For each feature classification, an allowed feature range is provided. This feature range may be a subset of a discrete set of possible feature classification values. The feature range also may be defined with a minimum and/or maximum.

With the method, impression models and/or ear scans may be automatically evaluated in order to give a "Go" or "No-Go" for a further manufacturing process based on impression quality and impression geometry. The method may find application in the order entry and/or scanning process and/or may detect, whether the received impression quality is sufficient for the ordered custom product. This may guarantee an improved efficiency and faster process execution.

The method may establish a time saving and a higher efficiency in the entire custom product manufacturing process. The quality of custom products in the hearing device market may be improvement. A cost reduction for the hearing device manufacture may be achieved.

According to an embodiment, the impression feature is an indicator applied to an ear impression after hardening of a material of ear impression inside the ear. It also may be that specific predefined point marks were applied on the ear impression by the hearing care specialist. These marks then also may be present in the impression model. For example, the scanner not only may be adapted to scan a surface of the ear impression, but also a color of the surface. It also may be that the mark is a small item attached to the ear impression at a predefined point.

According to an embodiment, the impression model is determined by scanning the human ear or scanning an impression taken from the human ear. Such an impression model may be made with a scanner adapted for scanning an ear channel and/or outer parts of a human ear.

According to an embodiment, the feature classification is selected from at least two values encoding a property of the impression feature. As already described, the feature classification may comprise solely two values (such as yes/no, ok, not ok, etc.), a set of discrete values, or a range of continuous values.

According to an embodiment, the method further comprises: receiving at least one design feature of a hearing device type; and comparing the design feature with the feature classification and determining, whether the hearing device type is adaptable to the human ear for which the impression model was made. The method not only may be used for checking an ear impression and/or an impression model but also for checking, whether the human ear is suitable for the hearing device that has been chosen for the human ear.

A design feature may be a possible range for a feature and/or geometric shape of a part of the hearing device. This range may be mapped and/or compared to a feature classification also related to the geometric shape of the hearing device. Examples for this are possible outer diameters of an in-the-ear hearing device and an ear channel diameter determined as feature classification from the impression model.

According to an embodiment, at least two impression models of the same human ear are made and/or received. The estimated shape model may be determined by adapting the statistical shape model to the at least two impression models. The impression models may be aligned with each other. This may improve the quality of the estimated shape model.

According to an embodiment, at least two impression models of ear impressions of the same human ear are received. For each impression model, an estimated shape model and a feature classification of the estimated shape model may be determined. A best usable ear impression and/or impression model may be determined from the feature classifications of the respective impression models. In such a way, a best ear impression and/or impression model that may be used for manufacturing may be selected.

According to an embodiment, the method may be performed by a scanner system with a scanner for generating the impression model. A feature classification determined by the scanner system may be output on a user interface of the scanner system. The method may provide a feedback for the hearing care specialist, whether the quality of the ear impression and/or the impression model is sufficient or not for the order. The values of the one or more feature classifications output on the user interface may explain what needs to be improved on the ear impression and/or impression model to achieve a needed quality. Furthermore, the hearing care specialist directly may see, whether the chosen hearing device is suitable for the ear.

Further aspects relate to a computer program for checking a usability of an impression model of a human ear, which, when being executed by a processor, is adapted to carry out the steps of the method as described in the above and in the following as well as to a computer-readable medium, in which such a computer program is stored.

For example, the computer program may be executed in a system, which scans an ear impression or the human ear itself to generate the impression model. The computer-readable medium may be a memory of this system. However, it also may be that the method is performed in a system, which solely receives the impression model and which generates manufacturing data for a hearing device.

In general, a computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code. The computer-readable medium may be a non-transitory or transitory medium.

A further aspect relates to a system for checking a usability of an impression model of a human ear, which system is adapted for performing the method as described above and below.

It has to be understood that features of the method as described in the above and in the following may be features of the computer program, the computer-readable medium and the system as described in the above and in the following, and vice versa.

These and other aspects will be apparent from and elucidated with reference to the embodiments described hereinafter.

FIG. 1 shows a system 10, which is adapted for manufacturing a hearing device based on an impression model 28. The system 10 comprises a scanner system 12 with a scanner 14 and a fitting device 20, which both may be arranged in the office of the hearing care specialist.

The impression model 28 may be made in the office of a hearing care specialist. The impression model 28 may be made from an ear impression 16. The hearing care specialist may fill a material in the ear channel and outer ear parts of an ear of a costumer, who wants to buy a hearing device with a customizable ear part.

The scanner 14 may be adapted for scanning the ear impression 16 and for generating an impression model 28 of the ear impression 16. It also may be that the scanner 14 is adapted for scanning parts of the human ear and the ear channel directly.

The fitting device 20, which is adapted for controlling the scanner 14, may send the impression model 28 to a manufacturing system 22, for example via internet. With the fitting device 20, also a hearing device may be fitted to a need of the customer by adjusting control parameters of the hearing device accordingly. This fitting may be performed with a user interface 21 of the fitting device 20.

Alternatively, it is also possible that the scanner system 12 is arranged at the site of the manufacturing system 22 and/or of the manufacture of the hearing device and that the ear impression 16 is sent via mail there.

The manufacturing system 22 comprises an evaluation device 24 and a manufacturing device 26. The evaluation device 24 receives the impression model 28 and determines, whether the ear impression 16 and/or the impression model 28 is suitable for manufacturing the hearing device as ordered by the customer. In this case, the evaluation device 24 instructs the manufacturing device 26, which may comprise a 3D printer, to produce the corresponding parts.

The method for checking a usability of the ear impression 16 and/or the impression model 28 as described herein may be performed by the evaluation device 24. It also may be that the fitting device 20 performs this method to show the hearing care specialist, whether he or she should make a new or further ear impression 16 and/or impression model 28, which may be better suited to be used in the manufacturing system 22.

Figure 2:
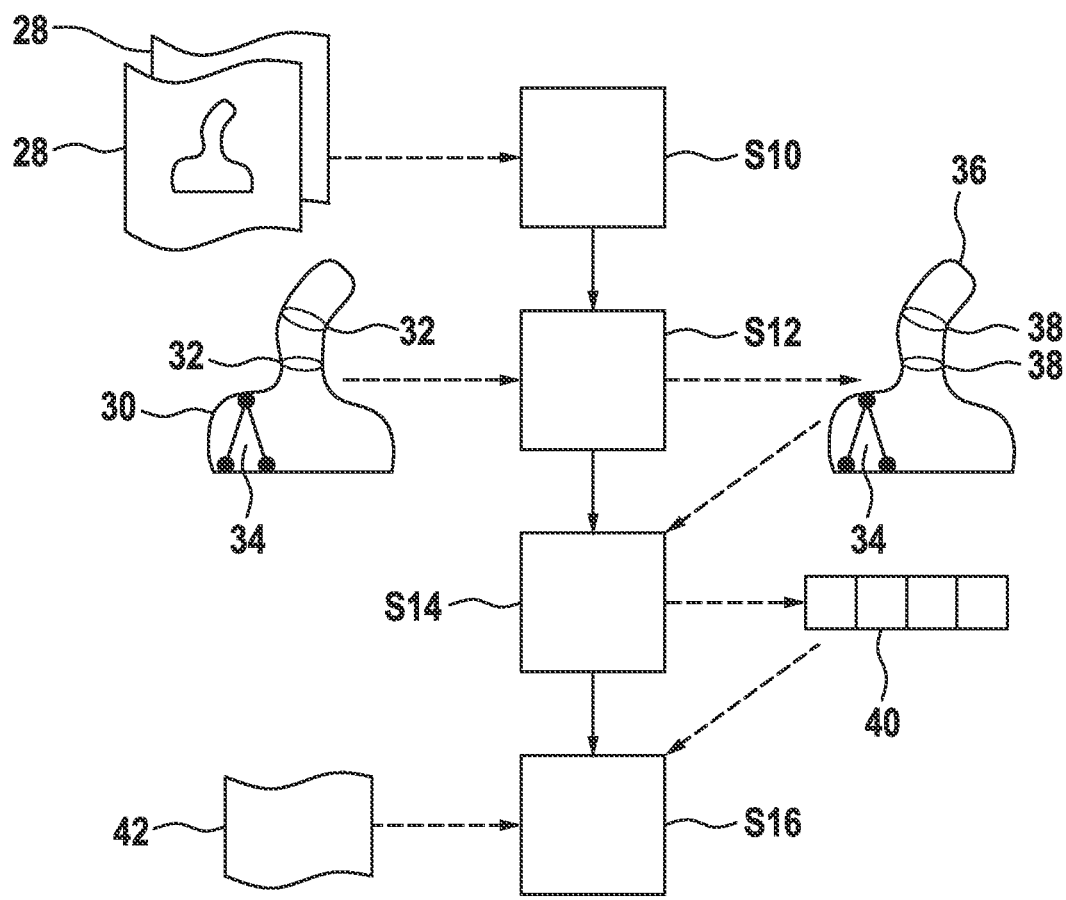
FIG. 2 shows a flow diagram for a method according to an embodiment.

FIG. 2 shows a flow diagram for a method for checking the usability of an ear impression 16 and/or an impression model 28 of a human ear. The method may be performed by the fitting device 20 and/or the evaluation device 24.

In step S10, one or more impression models 28 are received in the respective device 20, 24. The 3D impression models 28 may be made from one ear impression 16 or from several ear impressions. It also may be that some or all of the impression models 28 are made from a direct scan of an human ear. The impression models 28 may be files, which may be encoded in the STL format or in any other suitable file format representing a 3d model. For example, each impression model 28 may comprise a wire frame and/or 3D points.

In step S12, for each impression model 28, an estimated shape model 36 is determined by adapting a statistical shape model 30 to the impression model 28. This process also may be called Active Shape Model (ASM). It also may be that an estimated shape model 36 is determined by adapting a statistical shape model 30 to more than one impression model 28, which have been received in step S10.

As described above, this adaption process may be made deforming the statistical shape model 30 in a way that an objective function, which measures a difference between the impression model 28 and the deformed statistical shape model 30, is minimized. It may be that this objective function minimizes the differences to several impression models 28. For example, the objective function may determine a volume between the impression model 28 and the deformed statistical shape model 30. When this volume is 0, then the impression model 28 and the deformed statistical shape model 30 are considered to be equal. For the objective function also a point-to-surface distance metric may be used.

The statistical shape model 30 has been determined from a plurality of impression models of a plurality of human ears. The statistical shape model 30 may be seen as a model of the entity of human ears, comprising the average and the shape variation. All features of a human ear may be present in the statistical shape model 30. In the statistical shape model 30, additionally impression features 32 are encoded, which model such feature of the human ear. In the adaption process of the estimated shape model 36, the impression features 32 are mapped to estimate impression features 38.

The statistical shape model 30, the estimated shape model 36 may comprise a wire frame model 34, which may comprise 3D points and facets, which are defined by these points. These wire frame models 34 may define a surface of the human ear.

Figure 3:
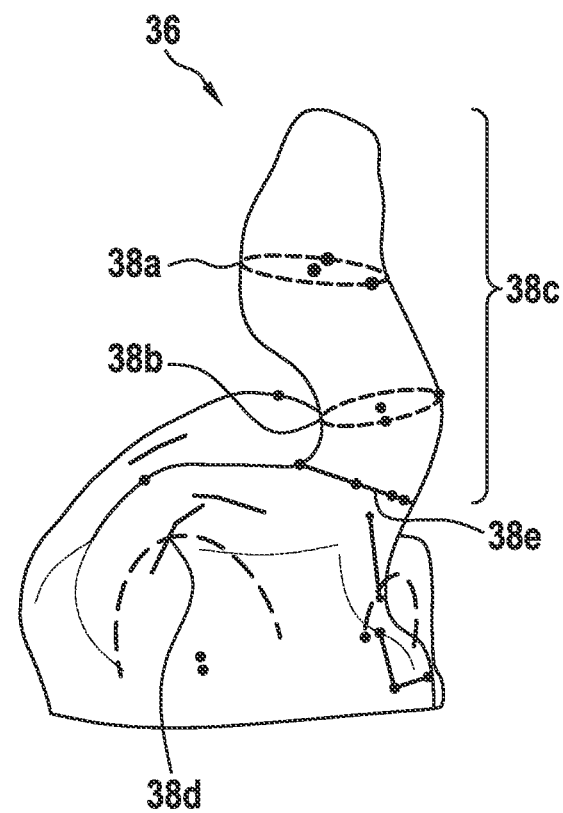
FIG. 3 shows an example of an estimated shape model and impression features detected with the method of FIG. 2.

FIG. 3 shows an example of an estimated shape model 36 that has been generated in step S12. The surface modelled by the estimated shape model 36 is depicted and also examples of impression features 38a-38e are shown.

The impression features 38a and 38b relate to a second bend and a first bend of the ear channel. The impression feature 38c relates to a canal length. The impression feature 38d relates to the concha. The impression feature 38e relates to an aperture plane of the ear channel.

Any feature which is covered in the range of the statistical shape model, for example any point between the concha and the second bend, can be detected on a particular ear by means of the active shape model (ASM). For example, for the impression features 38a, 38b, a radius, a cross section and/or a distance to the aperture plane 38 may be determined. The impression features 38a, 38b, 38c may comprise a geometric model of a geometric aspect of the estimated shape model 36. The impression features 38a-38e may be related to a part of the estimated shape model 36, which may be defined by a part of the wire frame. For example, specific points of the wire frame may be used for attaching a geometric shape, from which the geometric aspects may be determined. These points are derived from points of the statistical shape model 30, where the impression features have been defined.

In general, features such as aperture, bends, tragus, antitragus, crus, intertragal notch or anterior notch and there geometrical aspects may be determined from the estimated shape model 36.

It also may be that an impression feature 38 is determined from an indicator 18 applied to the ear impression 16 by the hearing care specialist. Such an indicator 18 may be an item attached to the ear impression 16 or a color mark.

In step S14, one or more feature classifications 40 are determined from the estimated impression features 38. The feature classification 40 for an impression feature 38 may be calculated with a predefined function from properties of the impression feature 38. For example, geometric aspects, such as radius, distances, position of the impression feature may be evaluated.

When all such geometric aspects are within specific ranges, the feature classification 40 may comprise "good impression". When at least one geometric aspect is out of bounds, then the feature classification 40 may comprise "bad impression". The feature classification 40 may be selected from at least two values encoding a property of the impression feature 38.

It also may be that the feature classification 40 comprises a range of classification values, such as "very poor concha", "poor concha", "good concha".

As a further example, it may be determined from the impression features 38, whether specific parts of the ear, which should be modelled with the impression model 28, are there or not there. Corresponding feature classifications 40 may be "canal missing", "canal missing first bend", "canal missing second bend", "helix missing", "helix partly missing", etc. Such missing parts for example may be determined by checking, whether specific parts of the estimated shape model 36 have a volume, surface, etc. which is larger than a minimal value.

In step S16, it is checked, whether the one or more feature classifications 40 are within allowed feature classification ranges. When this is the case, the corresponding impression model 28 is rated as usable. Such a classification range may comprise solely one value, such as "good impression". However, it also may be checked, whether specific feature classifications 40, which are related to geometric aspects, are larger than a minimum value and/or smaller than a maximum value.

When this is the case, the corresponding impression model 28 is rated as usable. A decision, whether the hearing device or the part of the hearing device, which is customizable, may be sent to the manufacturing device 26.

For example, a good impression is expected to comprise shape information including tragus/antitragus/concha up to the $2^{nd}$ bend of the ear canal. If the estimated impression feature 38 is too far away from a mean value and/or if the estimated impression feature 38 is classified as outlier, the impression may be rated with a bad quality and/or further manufacturing may be stopped.

When several estimated shape models 36 have been determined, a best usable ear impression 16 and/or impression model 28 may be selected based on the feature classifications 38 of the respective impression model 28.

It also may be that the method is additionally used for checking, whether a hearing device type, which has been selected by a costumer, can be customized to the ear of the costumer. To this end, at least one design feature 42 of the hearing device type may be received in step S16. The design feature 42 may be stored for the hearing device type in the fitting device 20 and/or in the evaluation device 24. The design feature 42 may be compared with the feature classification 40 and it may be determined, whether the hearing device type is adaptable to the human ear for which the impression model 28 was made.

In step S16, also the feature classification 38 may be output on the user interface 21. Also the check of the usability of the impression model 28 and/or the check of the customizability of the hearing device type may be output on the user interface 21. In such a way, the hearing care specialist can be directly notified, whether his ear impression 16 and/or the impression model 28 can be further processed in the manufacturing system 22, in particular with respect to the chosen hearing device type.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SYMBOLS

10 system
12 scanner system
14 scanner
16 ear impression
18 indicator/mark
20 fitting device
21 user interface
22 manufacturing system
24 evaluation device
26 manufacturing device
28 impression model
30 statistical shape model 32 impression feature
34 wire frame
36 estimated shape model
38 estimated impression feature
38a impression feature relating to second bend
38b impression feature relating to first bend
38c impression feature relating to canal length
38d impression feature relating to concha
38e impression feature relating to aperture plane
40 feature classification
42 design feature

What is claimed is:

1. A method for checking a usability of an impression model of a human ear and for manufacturing at least a part of a hearing device, the method comprising:
   determining the impression model by scanning the human ear or an ear impression of the human ear with a scanner;
   determining, by an evaluation device, an estimated shape model of the human ear by adapting a statistical shape model to the impression model, wherein the statistical shape model has been determined from a plurality of impression models of a plurality of human ears, wherein adapting the statistical shape model to the impression model is performed by deforming the statistical shape model such that an objective function, which measures a difference between the impression model and a deformed statistical shape model, is minimized, and wherein the statistical shape model has at least one impression feature, which is mapped in the adaption process of the impression model to the estimated shape model to an estimated impression feature of the estimated shape model;
   determining, by the evaluation device, a feature classification from the estimated impression feature; and
   when the feature classification is within an allowed feature classification range, rating, by the evaluation device, the impression model as usable; and
   manufacturing, by a manufacturing device, at least part of the hearing device based on the impression model when the impression model is rated as usable.

2. The method of claim 1, wherein the estimated impression feature comprises a part of the estimated shape model.

3. The method of claim 1, wherein the estimated impression feature comprises a geometric model of a geometric aspect of the estimated shape model.

4. The method of claim 1, wherein:
   the estimated impression feature is determined from an indicator applied to an ear impression after hardening of a material of the ear impression inside the human ear.

5. The method of claim 1, wherein:
   the impression model comprises a plurality of three-dimensional points indicating a surface of a human ear.

6. The method of claim 1, wherein the feature classification is selected from at least two values encoding a property of the impression feature.

7. The method of claim 1, wherein the statistical shape model has a plurality of impression features, which are mapped to estimated impression features, for which an impression classification is determined.

8. The method of claim 1, wherein:
   the estimated shape model comprises a wire frame model; and/or
   the impression feature comprises a wire frame model of a part of the impression model.

9. The method of claim 1, further comprising:
   receiving at least one design feature of a hearing device type;
   comparing the design feature with the feature classification and determining, whether the hearing device type is adaptable to the human ear for which the impression model was made.

10. The method of claim 1, wherein:
    at least two impression models of the same impression model are received; and
    the estimated shape model is determined by adapting the statistical shape model to the at least two impression models.

11. The method of claim 1, wherein:
    at least two impression models of ear impressions of the same human ear are received;
    for each impression model, an estimated shape model and a feature classification of the estimated shape model is determined; and
    a best usable impression model is determined from the feature classifications of the respective impression models.

12. The method of claim 1, wherein:
    the method is performed by a scanner system with a scanner for generating the impression model; and
    the method further comprising: outputting the feature classification on a user interface of the scanner system.

13. A non-transitory computer-readable medium storing a computer program for checking a usability of an impression model of a human ear and for manufacturing at least a part of a hearing device, which, when being executed by a processor, is adapted to carry out the steps of the method of claim 1.

14. A system for checking a usability of an impression model of a human ear and for manufacturing at least a part of a hearing device, the system comprising:
    a scanner system comprising a scanner configured to scan the human ear or an impression of the human ear and at least one computing device including a processor for generating the impression model based on the scan; and
    an evaluation device comprising at least one computing device including a processor configured to:
       determine an estimated shape model of the human ear by adapting a statistical shape model to the impression model, wherein the statistical shape model has been determined from a plurality of impression models of a plurality of human ears, wherein adapting the statistical shape model to the impression model is performed by deforming the statistical shape model such that an objective function, which measures a difference between the impression model and a deformed statistical shape model, is minimized, and wherein the statistical shape model has at least one impression feature, which is mapped in the adaption process of the impression model to the estimated shape model to an estimated impression feature of the estimated shape model;
       determine a feature classification from the estimated impression feature;
       when the feature classification is within an allowed feature classification range, rate the impression model as usable; and
       instruct a manufacturing device to manufacture at least a part of the hearing device based on the impression model when the impression model is rated as usable.

* * * * *